United States Patent
Ueda et al.

(10) Patent No.: US 10,307,523 B2
(45) Date of Patent: Jun. 4, 2019

(54) BLOOD PURIFICATION DEVICE

(71) Applicant: Nipro Corporation, Osaka (JP)

(72) Inventors: Mitsutaka Ueda, Osaka (JP);
Tomoyuki Matsumoto, Osaka (JP);
Shogo Okada, Osaka (JP); Hiroomi Nakano, Tokyo (JP)

(73) Assignee: Nipro Corporation, Osaka (JP)

( * ) Notice: Subject to any disclaimer, the term of this patent is extended or adjusted under 35 U.S.C. 154(b) by 222 days.

(21) Appl. No.: 15/123,349

(22) PCT Filed: Apr. 24, 2015

(86) PCT No.: PCT/JP2015/062588
§ 371 (c)(1),
(2) Date: Sep. 2, 2016

(87) PCT Pub. No.: WO2015/133653
PCT Pub. Date: Sep. 11, 2015

(65) Prior Publication Data
US 2017/0304517 A1    Oct. 26, 2017

(51) Int. Cl.
*A61M 1/16* (2006.01)
*A61M 1/34* (2006.01)
*F04B 23/04* (2006.01)
*F04B 9/02* (2006.01)
(Continued)

(52) U.S. Cl.
CPC ........ *A61M 1/1621* (2014.02); *A61M 1/1641* (2014.02); *A61M 1/3424* (2014.02); *F04B 9/02* (2013.01); *F04B 9/04* (2013.01); *F04B 23/04* (2013.01); *F04B 23/06* (2013.01)

(58) Field of Classification Search
CPC .............. A61M 1/1621; A61M 1/1641; A61M 1/3424; F04B 9/02; F04B 9/04; F04B 23/04; F04B 23/06
See application file for complete search history.

(56) References Cited

U.S. PATENT DOCUMENTS

| | | | | |
|---|---|---|---|---|
| 5,158,441 A | * | 10/1992 | Aid | ........................... F04B 7/06 417/500 |
| 2005/0013708 A1 | * | 1/2005 | Peeler | .................... B01L 3/0206 417/415 |
| 2016/0367743 A1 | * | 12/2016 | Jansson | ............... A61M 1/1615 |

FOREIGN PATENT DOCUMENTS

| | | |
|---|---|---|
| JP | S62-155859 A | 7/1987 |
| JP | H07-299133 A | 11/1995 |
| JP | 2001-234850 A | 8/2001 |

(Continued)

OTHER PUBLICATIONS

Extended European Search Report issued in European Application No. 15758837.7, dated Sep. 27, 2017.
(Continued)

*Primary Examiner* — Benjamin J Klein
(74) *Attorney, Agent, or Firm* — Marshall, Gerstein & Borun LLP

(57) ABSTRACT

In a blood purification device containing a blood purifier, a blood circuit, a blood pump, and a dialysate line having a fresh dialysate supply line and a used dialysate discharge line, a pair of plunger pumps are disposed in the dialysate line. The pair of plunger pumps are synchronized so that delivery of a fresh dialysate from one plunger pump and suction of a used dialysate into the other plunger pump simultaneously occur and the stroke of at least one of the pair of plunger pumps is made variable.

15 Claims, 11 Drawing Sheets

(51) Int. Cl.
  *F04B 9/04*     (2006.01)
  *F04B 23/06*    (2006.01)

(56) References Cited

FOREIGN PATENT DOCUMENTS

| | | |
|---|---|---|
| JP | 2001-248543 A | 9/2001 |
| JP | 3322987 B2 | 9/2002 |
| JP | 3328078 B2 | 9/2002 |
| JP | 2003-199820 A | 7/2003 |
| JP | 2007-222548 A | 9/2007 |
| WO | WO-2005044339 A2 | 5/2005 |

OTHER PUBLICATIONS

International Search Report issued in PCT/JP2015/062588 dated Jul. 21, 2015.

* cited by examiner

BLOOD PURIFICATION DEVICE

CROSS-REFERENCE TO RELATED APPLICATIONS

This application is a national stage application under 35 U.S.C. § 371 and claims the benefit of priority of international application no. PCT/JP2015/062588, filed Apr. 24, 2015, which claims the benefit of priority under 35 U.S.C. §. 119 of: Japanese patent application no. 2014-041441, filed Mar. 4, 2014; Japanese patent application no. 2014-101538, filed May 15, 2014; Japanese patent application no. 2014-109547, filed May 27, 2014; Japanese patent application no. 2014-109541, filed May 27, 2014; and Japanese patent application no. 2014-195371, filed Sep. 25, 2014, the entire contents of each being hereby incorporated herein by reference, in its entirety and for all purposes.

TECHNICAL FIELD

The presently described embodiments relate to a blood purification device in which a pair of plunger pumps are disposed in a dialysate line and a method for passing a dialysate to a blood purifier. More specifically, the presently described embodiments relate to a blood purification device which enables supply of a fresh dialysate without pulsation to a blood purifier and a method for passing a dialysate to a blood purifier, utilizing plunger pumps.

BACKGROUND

Heretofore, in order to improve serious states of patients with renal failure, patients developing hyperhydration due to chemical feeding after an operation, and the like, hemodialysis or blood filtration using a blood purification device has been performed. In order to supply a fresh dialysate to a blood purifier and discharge a used dialysate from a blood purifier, one utilizing a reciprocating pump capable of simultaneously performing the supply of a fresh dialysate and the discharge of a used dialysate is known heretofore (Patent Literature 1, Patent Literature 2).

Moreover, a plunger pump not requiring a valve for extracting the air in a dialysate has also been suggested as a reciprocating pump.

Known reciprocating pumps additionally require a water removing pump and a pressurization pump in order to perform water removal and backfiltration, and thus have posed a problem of an increase in cost. Other reciprocating pumps described previously do not simultaneously perform the supply of a fresh dialysate and the discharge of a used dialysate. Therefore, the reciprocating pumps need to be improved so as to simultaneously perform the supply of a fresh dialysate and the discharge of a used dialysate. Moreover, a plunger pump which enables the supply of a fresh dialysate without pulsation to a blood purification device has been desired.

SUMMARY OF DISCLOSURE

The present embodiments have been made in view of the above-described circumstances. It is an object of the present embodiments to provide a means simultaneously performing the supply of a fresh dialysate and the discharge of a used dialysate in a dialysate line.

It is another object of the present embodiments to provide a blood purification device capable of simultaneously performing the supply of a fresh dialysate and the discharge of a used dialysate to/from a dialysate line and supplying a fresh dialysate without pulsation to a blood purifier.

(1) A blood purification device contains a blood purifier, a blood circuit, a blood pump, and a dialysate line having a fresh dialysate supply line and a used dialysate discharge line, in which a pair of plunger pumps are disposed in the dialysate line, the pair of plunger pumps are synchronized so that delivery of a fresh dialysate from one plunger pump and suction of a used dialysate into the other plunger pump simultaneously occur, and the stroke of at least one of the pair of plunger pumps is made variable.

(2) As the pair of plunger pumps disposed in the dialysate line, one in which the pair of plunger pumps are disposed in a mirror-target manner with respect to a rotation shaft of a synchronization motor and are individually connected to the synchronization motor located in a central portion of the rotation shaft through drive joints is specifically employed.

(3) The stroke of the plunger pump on the fresh dialysate delivery side may be fixed and the adjustment of the stroke of the plunger pump on the used dialysate suction side may be performed by an angle adjustment motor adjusting the horizontal inclination angle between the plunger pumps and the rotation shaft of the synchronization motor.

(4) As the pair of plunger pumps disposed in the dialysate line, the rotation radius of the drive joint on the used dialysate suction side may be made larger than the rotation radius of the drive joint on the fresh dialysate delivery side and the stroke of the plunger pump on the used dialysate suction side may be made variable.

(5) A blood purification device according to the present embodiments has a blood purifier, a blood circuit connected to the blood purifier, a blood pump for generating blood flow in the blood circuit, a dialysate line having a fresh dialysate supply line and a used dialysate discharge line individually connected to the blood purifier, and plunger pumps individually provided in the fresh dialysate supply line and the used dialysate discharge line so as to form one pair. The plunger pump provided in the fresh dialysate supply line and the plunger pump provided in the used dialysate discharge line are synchronized so that the delivery of a fresh dialysate by the plunger pump provided in the fresh dialysate supply line and the suction of a used dialysate by the plunger pump provided in the used dialysate discharge line are simultaneously performed.

(6) The stroke of at least one of the plunger pumps individually provided in the fresh dialysate supply line and the used dialysate discharge line may be variable.

(7) The blood purification device further has a synchronization motor and drive joints which rotate by driving force given from the synchronization motor, in which the pair of plunger pumps may be disposed in a mirror-symmetrical manner with respect to the plane orthogonal to the rotation shaft of the synchronization motor and may be connected to the synchronization motor by the drive joints.

(8) In the plunger pump in which the stroke is variable of the pair of plunger pumps, the inclination angle of a shaft of a plunger with respect to the rotation shaft of the synchronization motor may be adjustable.

(9) An angle adjustment motor varying the inclination angle of the shaft of the plunger may be provided.

(10) The stroke of the plunger pump provided in the used dialysate discharge line may be variable.

(11) The rotation radius of the drive joint on the used dialysate suction side may be larger than the rotation radius of the drive joint on the fresh dialysate delivery side.

(12) The plunger pump may be a valveless plunger pump.

(13) Another pair of plunger pumps having a 180° shifted phase may be disposed in parallel to the dialysate line.

(14) The presently described embodiments relate to a method for passing a dialysate to a blood purifier using a first plunger pump and a second plunger pump individually provided in a fresh dialysate supply line and a used dialysate discharge line individually connected to the blood purifier. The method for passing a dialysate to the blood purifier includes a delivery step of delivering a fresh dialysate to the blood purifier through the fresh dialysate supply line by transmitting rotary drive to the first plunger pump from the synchronization motor and a suction step of sucking a used dialysate from the blood purifier through the used dialysate discharge line by transmitting rotary drive to the second plunger pump from the synchronization motor, in which the delivery step and the suction step are simultaneously performed in a synchronized manner.

Thus, the supply of a fresh dialysate and the discharge of a used dialysate to/from the blood purifier can be simultaneously performed using the plunger pumps.

(15) Preferably, the transmission of the drive of the synchronization motor to the first plunger pump in the delivery step and the transmission of the drive of the synchronization motor to the second plunger pump in the suction step are performed at a 180° shifted phase.

Thus, the phase of the pulsation generated when a fresh dialysate is supplied to the blood purifier by the first plunger pump and the phase of the pulsation generated when a used dialysate is discharged from the blood purifier by the second plunger pump are synchronized, so that the pressure of the dialysate in the blood purifier is stabilized.

(16) Preferably, the stroke of the first plunger pump in the delivery step and the stroke of the second plunger pump in the suction step are differentiated from each other.

Thus, backfiltration of blood or removal of water from blood can be performed in the blood purifier.

(17) A blood purification device according to the present embodiments has a blood purifier, a blood circuit connected to the blood purifier, a blood pump for generating blood flow in the blood circuit, a dialysate line having a fresh dialysate supply line and a used dialysate discharge line which are individually connected to the blood purifier so as to be at least partially in parallel to each other, and a pair of plunger pumps provided in each of the parallel fresh dialysate supply line and the parallel used dialysate discharge line. The pair of plunger pumps individually provided in the parallel fresh dialysate supply lines alternately and continuously perform the delivery of a fresh dialysate by one plunger pump of the pair of plunger pumps and the delivery of a fresh dialysate by the other plunger pump. The pair of plunger pumps provided in the parallel used dialysate discharge lines alternately and continuously perform the suction of a used dialysate by one plunger pump of the pair of plunger pumps and the suction of a used dialysate by the other plunger pump. The pair of plunger pumps provided in the fresh dialysate supply line and the pair of plunger pumps provided in the used dialysate discharge line are synchronized so that the delivery of a fresh dialysate by the pair of plunger pumps provided in the fresh dialysate supply line and the suction of a used dialysate by the pair of plunger pumps provided in the used dialysate discharge line are simultaneously performed.

In the pair of plunger pumps of the parallel fresh dialysate supply line, the delivery of a fresh dialysate from one plunger pump and the delivery of a fresh dialysate from the other plunger pump are alternately and continuously performed. In the pair of plunger pumps of the parallel used dialysate discharge line, the suction of a used dialysate into one plunger pump and the suction of a used dialysate to the other plunger pump are alternately and continuously performed. Further, the plunger pumps are synchronized so that the delivery of a fresh dialysate and the suction of a used dialysate simultaneously occur. Therefore, the supply of a fresh dialysate to the blood purifier and the discharge of a used dialysate from the blood purifier are simultaneously performed. Thus, a fresh dialysate without pulsation is supplied to the blood purifier.

(18) Preferably, the stroke of at least one of the pair of plunger pumps provided in the parallel used dialysate discharge lines is variable.

Thus, when the strokes are adjusted so that the strokes of the plunger pumps provided in the used dialysate discharge line are smaller than the strokes of the plunger pumps provided in the fresh dialysate supply line, backfiltration can be performed in the blood purifier. When the strokes are adjusted so that the strokes of the plunger pumps provided in the used dialysate discharge line are larger than the strokes of the plunger pumps provided in the fresh dialysate supply line, water removal can be performed in the blood purifier.

(19) Preferably, a synchronization motor and a first drive joint which rotates by driving force given from the synchronization motor are further provided, and the pair of plunger pumps provided in the parallel fresh dialysate supply lines are disposed in a mirror-symmetrical manner with respect to the plane orthogonal to the rotation shaft of the synchronization motor and are connected to the synchronization motor by the first drive joint.

The pair of plunger pumps are disposed in a mirror-symmetrical manner with respect to the plane orthogonal to the rotation shaft of the synchronization motor and are individually connected to the rotation shaft of the synchronization motor via the first drive joint, and therefore the pair of plunger pumps have a relationship in which the phases are 180° shifted. Therefore, even when the phases of the pair of plunger pumps are not adjusted, the supply of a fresh dialysate to the blood purifier can be alternately and continuously performed.

(20) Preferably, a synchronization motor and a second drive joint which rotates by driving force given from the synchronization motor are further provided, and the pair of plunger pumps provided in the parallel used dialysate discharge lines are disposed in a mirror-symmetrical manner with respect to the plane orthogonal to the rotation shaft of the synchronization motor and are connected to the synchronization motor by the second drive joint.

The pair of plunger pumps are disposed in a mirror-symmetrical manner with respect to the plane orthogonal to the rotation shaft of the synchronization motor and are individually connected to the rotation shaft of the synchronization motor via the second drive joint, and therefore the pair of plunger pumps have a relationship in which the phases are 180° shifted. Thus, even when the phases of the pair of plunger pumps are not adjusted, the discharge of a used dialysate from the blood purifier can be alternately and continuously performed.

(21) Preferably, the pair of plunger pumps provided in the parallel fresh dialysate supply lines and the pair of plunger pumps provided in the parallel used dialysate discharge lines are disposed in a mirror-symmetrical manner with respect to the plane orthogonal to the rotation shaft of the synchronization motor.

Thus, the pair of plunger pumps have a relationship in which the phases are 180° shifted. Therefore, even when the phases of the pair of plunger pumps are not adjusted, the supply of a fresh dialysate to the blood purifier and the discharge of a used dialysate from the blood purifier can be simultaneously performed.

(22) Preferably, a synchronization motor and a second drive joint which rotates by driving force given from the synchronization motor are further provided, and the pair of plunger pumps provided in the parallel used dialysate discharge lines are connected to the synchronization motor by the second drive joint and, in the plunger pump in which the stroke is variable of the pair of plunger pumps individually provided in the parallel used dialysate discharge lines, the inclination angle of a shaft of a plunger with respect to the rotation shaft of the synchronization motor is adjustable.

The stroke of the plunger pump provided in the used dialysate discharge line can be adjusted by adjusting the inclination angle between the plunger pump and the rotation shaft of the synchronization motor.

(23) Preferably, an angle adjustment motor varying the inclination angle of the shaft of the plunger is further provided.

Thus, also when the plunger pump is driven, the inclination angle of the shaft of the plunger can be adjusted.

As described above, the present embodiments are generally described and can be further understood by referring to some specific examples. These examples are presented herein for purposes of illustration, and not limited unless otherwise specified.

According to the present embodiments, supply of a fresh dialysate to a blood purifier and discharge of a used dialysate can be simultaneously performed.

Moreover, a blood purification device in which a pair of plunger pumps capable of performing water removal and backfiltration are disposed is realized.

Moreover, supply of a fresh dialysate and discharge of a used dialysate can be simultaneously performed to a dialysate line and a fresh dialysate without pulsation can be supplied to a blood purifier.

DETAILED DESCRIPTION

Hereinafter, in order to further specify the that which is presently described, embodiments are described with reference to the drawings.

First Embodiment

Figure 1:
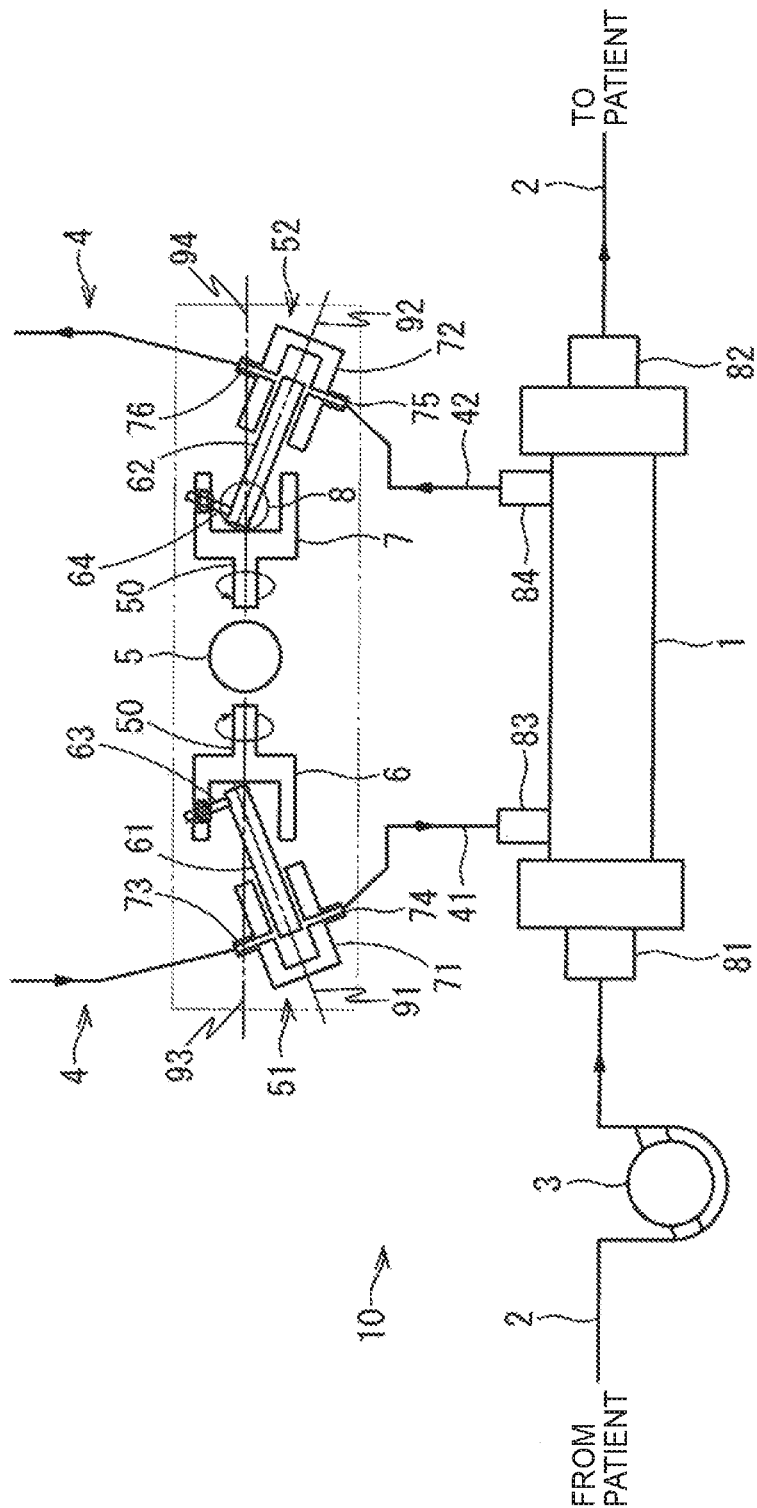
FIG. 1 is a schematic explanatory view of a blood purification device 10 according to a first embodiment.
Figure 2:
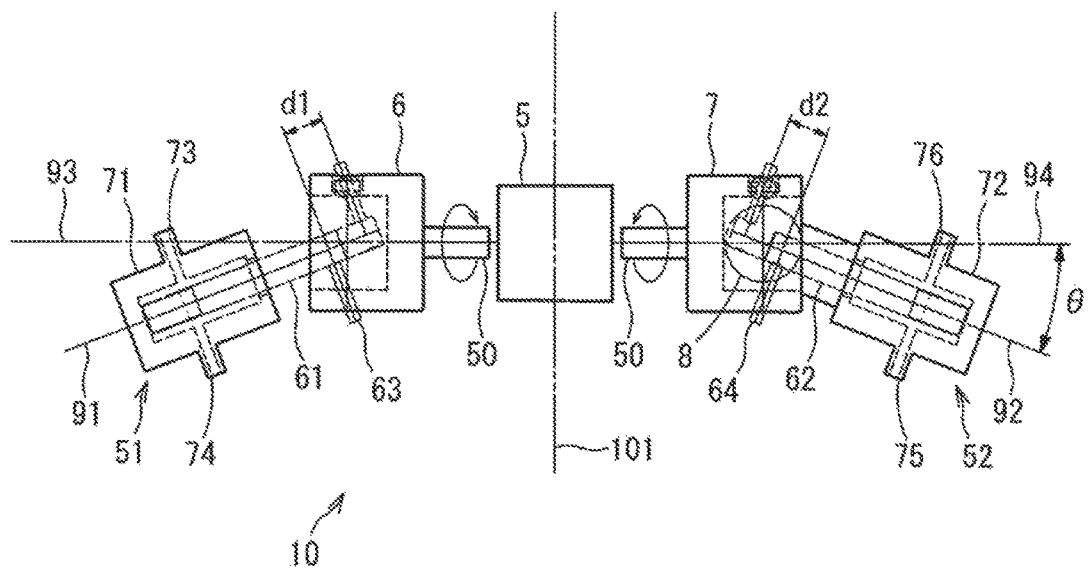
FIG. 2 is a schematic plan view illustrating the configuration in the vicinity of plunger pumps 51 and 52.
Figure 3:
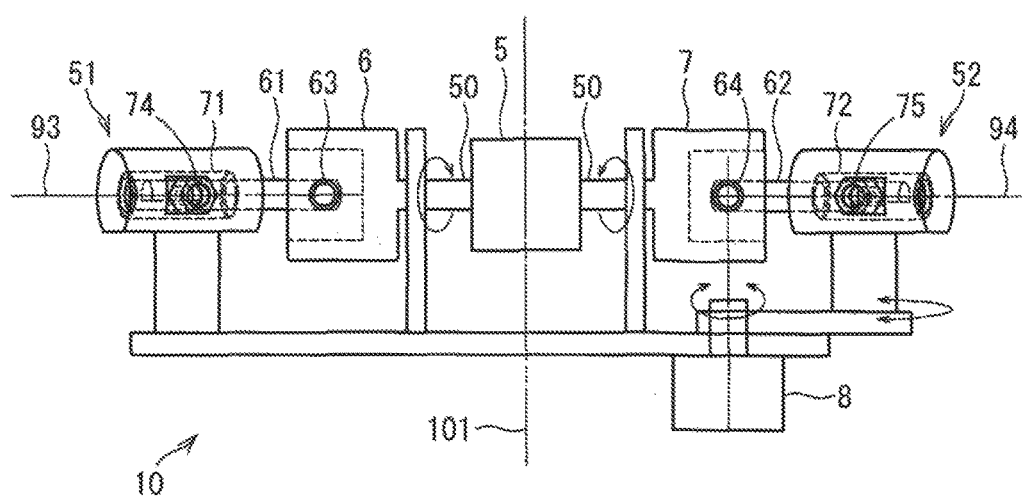
FIG. 3 is a schematic side view illustrating the configuration in the vicinity of the plunger pump 51 and 52.

FIG. 1 illustrates a schematic explanatory view illustrating a first embodiment. FIG. 2 and FIG. 3 illustrates a schematic plan view and a schematic side view, respectively, illustrating one example of the plunger pump of FIG. 1.

A blood purification device 10 contains a blood purifier 1, a blood circuit 2, a blood pump 3, and a dialysate line 4 having a fresh dialysate supply line 41 and a used dialysate discharge line 42 as illustrated in FIG. 1. In the dialysate line 4, a pair of plunger pumps 51 and 52 are disposed.

The blood purifier 1 is a container which has a first port 81, a second port 82, a third port 83, and a fourth port 84 for inflow and outflow of blood and a dialysate and the inside of which is filled with hollow fibers. Due to the fact that blood is caused to pass through the internal space of the hollow fibers through the first port 81 and the second port 82 and a dialysate is caused to pass through the outside of the hollow fibers through the third port 83 and the fourth port 84, removal of water from blood or backfiltration is performed.

The blood circuit 2 is connected to the first port 81 and the second port 82. The blood circuit 2 forms a blood flow passage containing a resin tube or the like and leads blood flowing out of a blood vessel of a patient to the blood purifier 1 and leads blood flowing out of the blood purifier 1 to a blood vessel of a patient. The blood circuit 2 is provided with the blood pump 3 for generating blood flow in the blood circuit 2. For the blood pump 3, known substances, such as a tube pump, may be employed.

The dialysate line 4 is connected to the third port 83 and the fourth port 84 of the blood purifier 1. The dialysate line 4 forms a dialysate flow passage containing a resin tube or the like. The fresh dialysate supply line 41 is connected to the third port 83 of the blood purifier 1 and the used dialysate discharge line 42 is connected to the fourth port 84 of the blood purifier 1. Although not illustrated in each figure, the other end of the fresh dialysate supply line 41 is connected to a tank in which a fresh dialysate is stored and the other end of the used dialysate discharge line 42 is connected to a waste tank storing a used dialysate.

The plunger pump 51 is disposed in the fresh dialysate supply line 41. The plunger pump 52 is disposed in the used dialysate discharge line 42.

To the pair of plunger pumps 51 and 52, rotation is transmitted from a rotation shaft 50 of a synchronization motor 5 through drive joints 6 and 7. The drive joints 6 and 7 are connected to one end side of plungers 61 and 62 of the plunger pumps 51 and 52, respectively. The plungers 61 and 62 reciprocate in cylinders 71 and 72 by drive transmitted from the drive joints 6 and 7, respectively.

Axial directions 91 and 92 of the plungers 61 and 62 incline (cross) with respect to axial directions 93 and 94 of the drive joints 6 and 7, respectively. In this embodiment, the axial directions 93 and 94 of the drive joints 6 and 7 are the same as the axial direction of a rotation shaft 50. The strokes of the plungers 61 and 62 which reciprocate by drive transmitted from the drive joints 6 and 7, respectively, are determined depending on the inclination angle θ between the axial directions 91 and 92 of the plungers 61 and 62 and the axial directions 93 and 94 of the drive joints 6 and 7, respectively. More specifically, when the inclination angle θ is large, the strokes of the plungers 61 and 62 become large and, when the inclination angle θ is small, the strokes of the plungers 61 and 62 become small.

A pair of ports 73 and 74 or a pair of ports 75 and 76 communicating with the internal space are provided in cylinders 71 and 72, respectively. The pair of ports 73 and 74 and the pair of ports 75 and 76 are disposed at positions different by 180° with respect to the axial directions of the cylinders 71 and 72, respectively, i.e., axial symmetry. Although not illustrated in detail in each figure, the plungers 61 and 62 have a columnar shape sealing the cylinder 71 and 72, respectively, in a fluid-tight manner and the half including the axis line of the columnar shape on the tip side (other end side which is not connected to the drive joints 6 and 7) is notched. Due to the fact that the notched portions rotate in the cylinders 71 and 72, one of the pair of ports 73 and 74 or the pair of ports 75 and 76 of the cylinders 71 and 72 is sealed by the plungers 61 and 62, respectively, and the other port is opened by the notched portion.

As illustrated in FIGS. 1 to 3, the one pair of plunger pumps 51 and 52 have a mirror-symmetrical structure with respect to the plane (plane orthogonal to the sheet of FIGS. 1 to 3) orthogonal to the rotation shaft 50 of the synchronization motor 5. In detail, as illustrated in FIGS. 2 and 3, the plunger pumps 51 and 52 have a mirror-symmetrical structure with respect to a plane 101 orthogonal to the rotation shaft 50 of the synchronization motor 5 and including the middle in a direction along the axial directions 93 and 94 of the drive joints 6 and 7, respectively. Therefore, the angles at which the plungers 61 and 62 incline with respect to the drive joints 6 and 7, respectively, when the angles θ are the same, the positions of the ports 73, 74, 75, and 76 of the cylinders 71 and 72, respectively, and the like are in a mirror-symmetrical state.

As the mirror-symmetrical structure, the structures of the plungers 61 and 62 and the cylinders 71 and 72 are in a mirror-symmetrical state. However, a state where, by making the angle θ variable, the axial directions 91 and 92 of the plungers 61 and 62 of the plunger pumps 51 and 52, respectively, are not in a mirror-symmetrical state and a state where, due to the fact that the rotation radii of the drive joints 6 and 7 are different from each other, a strict mirror-symmetrical state is not achieved are not excluded from the mirror-symmetrical structure. More specifically, the mirror-symmetrical structure is to be understood as follows: insofar as a relationship in which the phases of the pair of plunger pumps 51 and 52 are 180° shifted can be maintained when the pair of plunger pumps 51 and 52 are connected through the drive joints 6 and 7, respectively, so as to be rotated by the same synchronization motor 50, it is permitted that the angles, the rotation radii, and the like are different from each other in the pair of plunger pumps 51 and 52.

Thus, the phases of the plunger pumps 51 and 52 are different from each other by 180° with respect to the rotation of the drive joints 6 and 7. More specifically, the plunger pump 52 is sucking a fresh dialysate while the plunger pump 51 is delivering a fresh dialysate and the plunger pump 52 is delivering a fresh dialysate while the plunger pump 51 is sucking a fresh dialysate. Thus, the pair of plunger pumps 51 and 52 simultaneously perform the delivery of a fresh dialysate by the plunger pump 51 and the delivery of a fresh dialysate by the plunger pump 52 in a synchronized manner.

Due to the fact that the plungers 61 and 62 reciprocate in the cylinders 71 and 72 in the plunger pumps 51 and 52, respectively, a fresh dialysate is delivered in the plunger 51 and a used dialysate is sucked in the plunger 52. Since the uniform rotation of the synchronization motor 50 is transmitted as the stroke of each plunger 61 and 62 by the drive joints 6 and 7, respectively, the movement speed of each of the plungers 61 and 62 forms a sin curve or a cos curve with respect to the rotation phase of the drive joints 6 and 7, respectively. Therefore, the delivery amount of a fresh dialysate by the plunger 51 and the suction amount of a used dialysate by the plunger 52 form a sin curve or a cos curve. The fluctuation of the delivery amount of a fresh dialysate by the plunger 51 and the fluctuation of the suction amount of a used dialysate by the plunger 52 represented by such a sin curve or a cos curve are referred to as "pulsation" in this specification. Since the delivery of a fresh dialysate by the plunger pump 51 and the delivery of a fresh dialysate by the plunger pump 52 are simultaneously performed in a synchronized manner, the "pulsation" thereof simultaneously arise in a synchronized manner.

The pair of plunger pumps 51 and 52 are synchronized so that the delivery of a fresh dialysate from the plunger pump 51 (delivery step) and the suction of a used dialysate into the plunger pump 52 (suction step) simultaneously occur, and the stroke of at least one of the pair of plunger pumps 51 and 52 is made variable. Therefore, the supply of a fresh dialysate to the blood purifier 1 and the discharge of a used dialysate from the blood purifier 1 can be simultaneously performed. When a stroke d1 of the plunger pump 51 on the fresh dialysate delivery side is made larger than a stroke d2 of the plunger pump 52 on the used dialysate suction side, backfiltration can be performed. When the stroke d1 of the plunger pump 51 on the fresh dialysate delivery side is made smaller than the stroke d2 of the plunger pump 52 on the used dialysate suction side, water removal can be performed.

Specifically, as the pair of plunger pumps 51 and 52, the pair of plunger pumps 51 and 52 are disposed in a mirror-target manner with respect to the rotation shaft 50 of the synchronization motor 5 and are connected to the synchronization motor 5 located in the central portion of the rotation shaft 50 through the drive joints 6 and 7, respectively, as illustrated in FIG. 2 and FIG. 3, for example.

Figure 4:
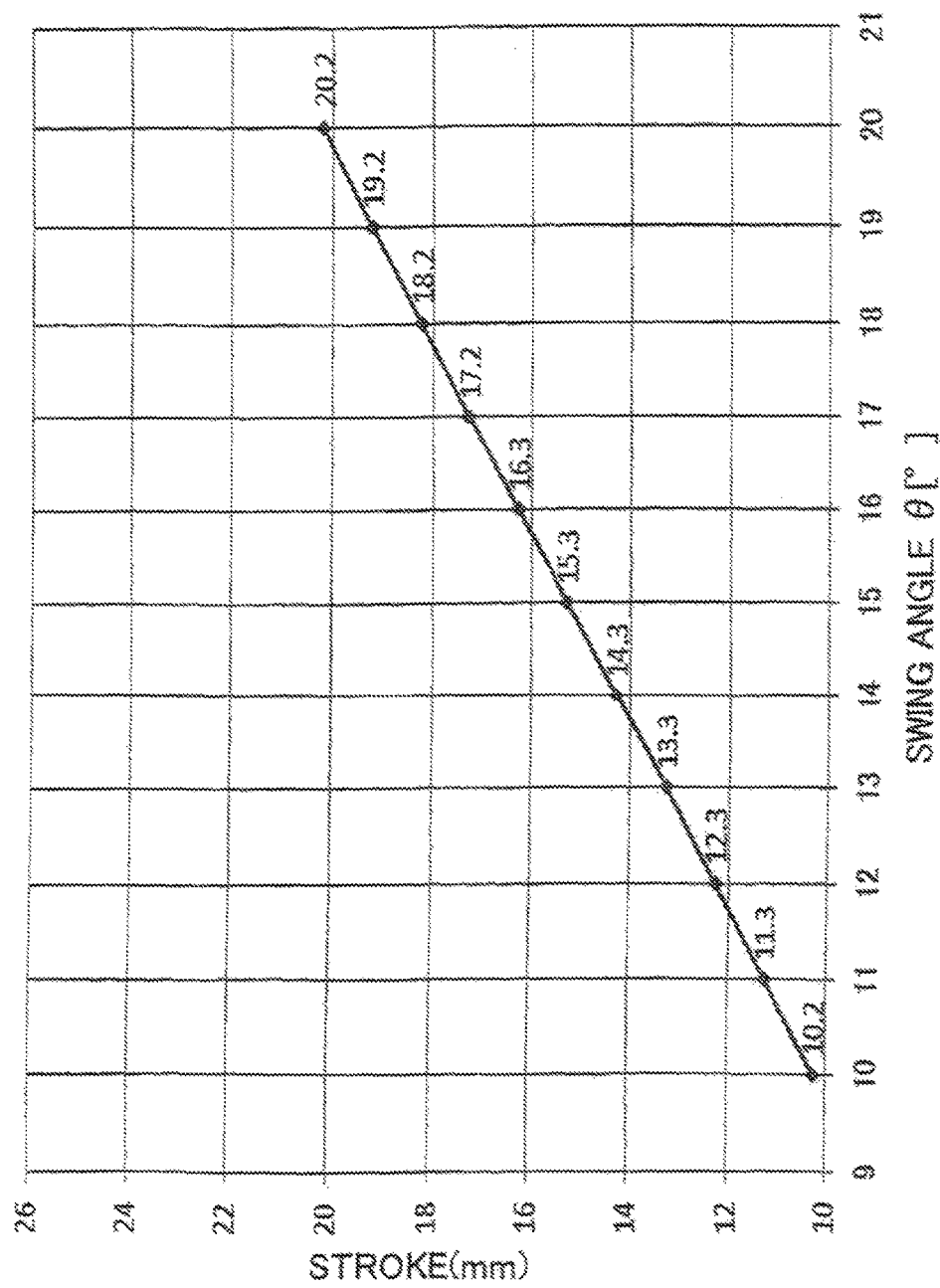
FIG. 4 is a diagram showing the relationship between the swing angle θ and the stroke d2 of the plunger pump 52 (Drive radius of 29.5 mm).

This embodiment is configured so that the stroke d1 of the plunger pump 51 is fixed, the stroke d2 of the plunger pump 52 is made variable, and the adjustment of the stroke d2 of the plunger pump 52 is performed by the angle adjustment motor 8 adjusting the horizontal inclination angle θ between the axial direction 91 of the plunger pump 52 and the rotation shaft 94 of the synchronization motor 5. Herein, the inclination angle θ can be adjusted so that the stroke d2 can be made larger or can be made smaller than the stroke d1 as illustrated in FIG. 4. When the inclination angle θ is made larger, the stroke becomes larger. When the inclination angle θ is made smaller, the stroke becomes smaller. In this connection, when the relationship between the stroke and the delivery amount of the plunger pump when the plunger diameter was 16 mm was determined, the delivery amount per 1 mm stroke was about 24.1 cc/min.

Herein, the adjustment function of the inclination angle of the plunger pump is described in a little more detail. More specifically, the drive joints 6 and 7 are provided with a bearing socket. To the bearing socket, a bearing is attached. The bearings each are provided with a through-hole in the central portion. One end of operation shafts 63 and 64 extending from the plungers 61 and 62 of the plunger pumps 51 and 52, respectively, is slidably inserted into and passed through the through-holes. This embodiment is configured so that the operation shafts 63 and 64 are fixed so that that the other end thereof is perpendicular to the surface of the plungers 61 and 62, respectively, and that the rotation of the synchronization motor 5 is transmitted to the drive joints 6 and 7, the rotation of the drive joints 6 and 7 is transmitted to the plungers 61 and 62 by the operation shafts 63 and 64, respectively, and the stroke d1 and d2 are generated in the inclined plunger pumps 51 and 52, respectively. Therefore, the plungers 61 and 62 are configured so as to reciprocate according to the stroke d1 and d2 while rotating in the cylinders 71 and 72, respectively.

The arrangement manner of the pair of plunger pumps 51 and 52 with respect to the rotation axes of the drive joints 6 and 7 and the rotation shaft 50 of the synchronization motor 5 is not limited. In any case, in order to simultaneously cause the delivery of a fresh dialysate from the plunger pump 51 and the suction of a used dialysate into the plunger pump, the phases of the plunger pumps 51 and 52 need to be 180° shifted.

Figure 5:
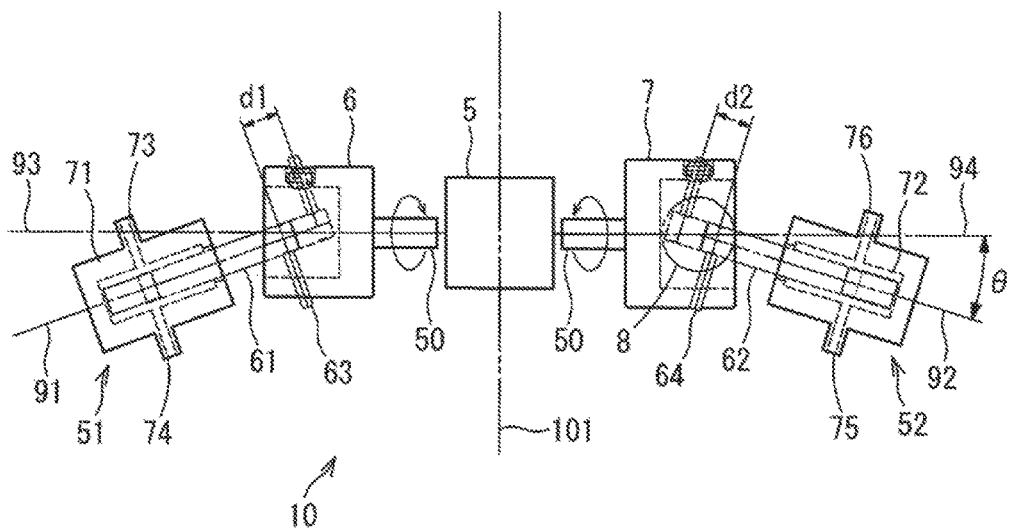
FIG. 5 is a schematic plan view illustrating a modification of the plunger pumps 51 and 52.
Figure 6:
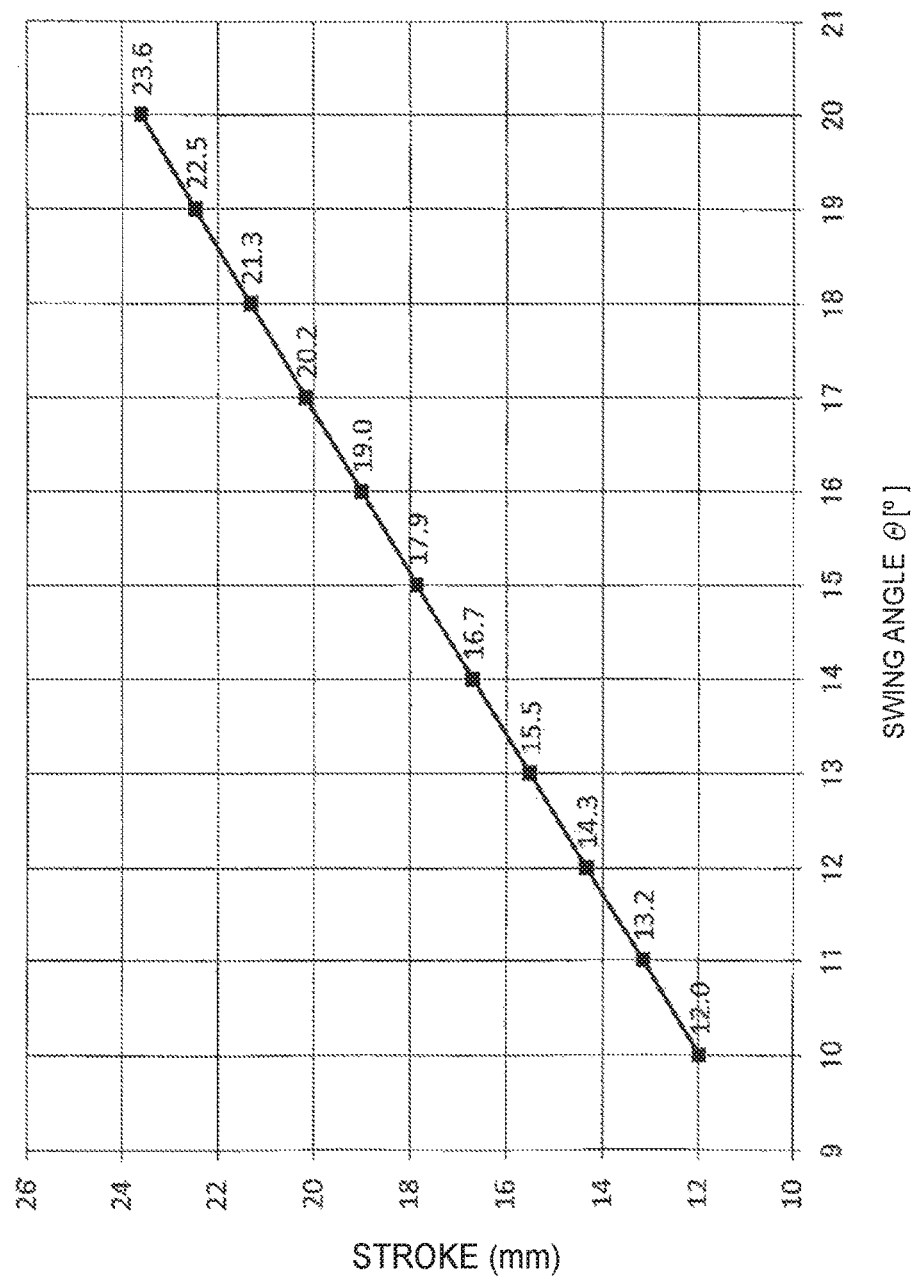
FIG. 6 is a diagram showing the relationship between the swing angle θ and the stroke d2 of the plunger pump 52 in a modification of the first embodiment (Drive radius of 34.5 mm).

As the pair of plunger pumps 51 and 52 disposed in the dialysate line 4, the rotation radius of the drive joint 7 on the used dialysate suction side may be made larger than the rotation radius of the drive joint 6 on the fresh dialysate delivery side and the stroke d2 of the plunger pump 52 on the used dialysate suction side may be made variable as illustrated in FIG. 5. When configured as described above, the stroke d2 of the plunger pump 52 on the used dialysate suction side can be greatly varied as illustrated in FIG. 6. Therefore, when the suction amount corresponding to the delivery amount of the plunger pump 51 is set, the inclination angle θ of the plunger pump 52 can be made smaller than the inclination angle of the plunger pump 51, and thus the adjustment of the inclination angle θ of the plunger pump 52 is facilitated.

As the plunger pumps 51 and 52, a valveless plunger pump may be employed. In this case, a valve for extracting the air in a dialysate may not be separately prepared, and therefore the economical efficiency is achieved.

Operational Effects of First Embodiment

According to the first embodiment, the pair of plunger pumps 51 and 52 disposed in the dialysate line 4 are synchronized so that the delivery of a fresh dialysate from the plunger pump 51 and the suction of a used dialysate into the plunger pump 52 simultaneously occur, and therefore the supply of a fresh dialysate to the blood purifier 1 and the discharge of a used dialysate from the blood purifier 1 can be simultaneously performed.

Moreover, the stroke of the plunger pump 52 is made variable, and therefore, when the stroke d1 of the plunger pump 51 is made larger than the stroke d2 of the plunger pump 52, backfiltration can be performed and, when the stroke d1 of the plunger pump 51 is made smaller than the stroke d2 of the plunger pump 52, water removal can be performed.

Moreover, the pair of plunger pumps 51 and 52 are disposed in a mirror-target manner on the rotation shaft 50 of the synchronization motor 5 and are connected through the drive joints 6 and 7 so as to be rotated by the same synchronization motor 5, and therefore, the pair of plunger pumps 51 and 52 have a relationship in which the shifts are 180° shifted from the beginning, and, even when the shifts thereof are not adjusted, the supply of a fresh dialysate to the blood purifier 1 and the discharge of a used dialysate from the blood purifier can be simultaneously performed.

Moreover, the stroke d1 of the plunger pump 51 is fixed and the horizontal angle θ of the plunger pump 52 is variable with respect to the rotation shaft 50 of the synchronization motor 5 by the angle adjustment motor 8, and therefore the stroke d2 of the plunger pump 52 can be adjusted by varying the horizontal angle θ of the plunger pump 52 to be made larger or to be made small than the stroke d1 of the plunger pump 51. Therefore, backfiltration or water removal can be performed by adjusting the stroke d2 of the plunger pump 52.

Moreover, the rotation radius of the drive joint 7 is made larger than the rotation radius of the drive joint 6, and therefore the stroke d2 of the plunger pump 52 can be greatly varied, so that the angle adjustment of the plunger pump 52 is facilitated (A smaller inclination angle is acceptable.). Moreover, as compared with a case where the drive joints 6 and 7 of both the plunger pumps 51 and 52 are made to have the same size, a large backfiltration amount and a large water removal amount can be set.

Moreover, a valveless plunger pump is employed as the plunger pumps 51 and 52, and therefore a valve for extracting the air in a dialysate can be omitted.

The plunger pumps 51 and 52 are preferably formed with glass. The plungers 61 and 62 and the cylinders 71 and 72 each are preferably manufactured using shrinking processing. Due to the fact that the plunger pumps 51 and 52 are manufactured from glass, the sealability in the plunger pumps 51 and 52 can be secured even when the tolerance of the inner diameter of the cylinders 71 and 72 to the outer diameter of the plungers 61 and 62 is large to some extent, and therefore the mass productivity of the plunger pumps 51 and 52 is improved. In each of the plunger pumps 51 and 52, both the plungers 61 and 62 and the cylinders 71 and 72 are preferably formed with glass. Materials of the plunger pumps 51 and 52 are not limited to glass and the plunger pumps 51 and 52 may be formed with other materials, such as ceramics. A method for manufacturing the plungers 61 and 62 and the cylinders 71 and 72 is not limited to the method employing shrinking processing.

The delivery step of delivering a fresh dialysate to the blood purifier 1 through the fresh dialysate supply line 41 by transmitting rotational drive to the plunger pump 51 from the synchronization motor 50 and the suction step of sucking a used dialysate from the blood purifier 1 through the used dialysate discharge line 42 by transmitting rotational drive to the plunger pump 52 from the synchronization motor 50 are simultaneously performed in a synchronized manner, and therefore the supply of a fresh dialysate and the discharge of a used dialysate to/from the blood purifier 1 can be simultaneously performed using the pair of plunger pumps 51 and 52.

Moreover, the transmission of the drive of the synchronization motor 50 to the plunger pump 51 and the transmission of the drive of the synchronization motor 50 to the plunger pump 52 are performed at a 180° shifted phase, and therefore the phase of the pulsation generated when supplying a fresh dialysate to the blood purifier 1 by the plunger pump 51 and the phase of the pulsation generated when discharging a used dialysate from the blood purifier 1 by the plunger pump 52 are synchronized, so that the pressure of the dialysate in the blood purifier 1 is stabilized.

Moreover, by differentiating the stroke d1 of the plunger pump 51 and the stroke d2 of the plunger pump 52 from each other, backfiltration of blood or removal of water from blood can be performed in the blood purifier 1.

Second Embodiment

Figure 7:
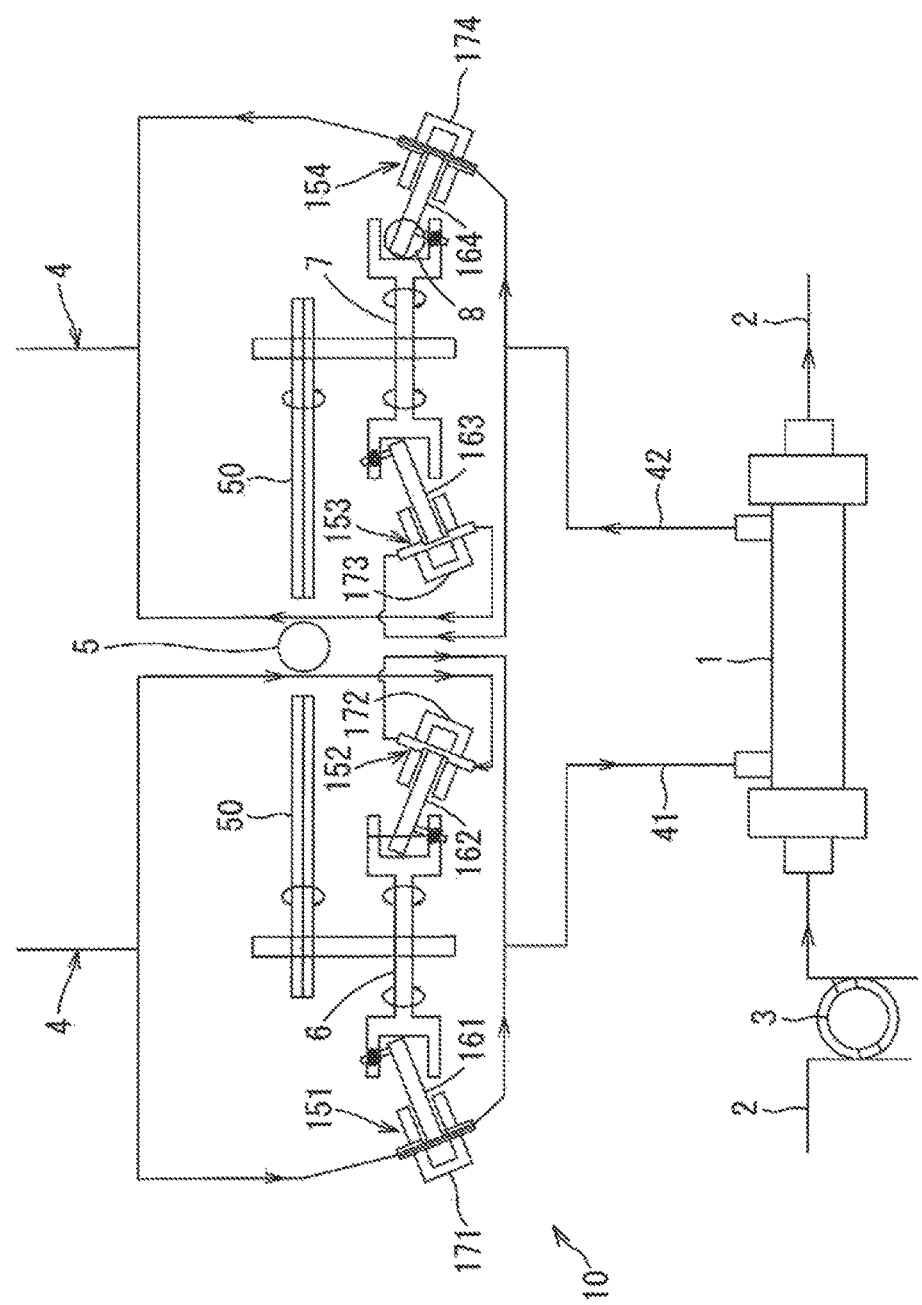
FIG. 7 is a schematic view illustrating the structure of a blood purification device 10 according to a second embodiment.

As illustrated in FIG. 7, a blood purification device 11 has a blood purifier 1, a blood circuit 2 connected to the blood purifier 1, a blood pump 3 generating blood flow in the blood circuit 2, a dialysate line 4 having a fresh dialysate supply line 41 and a used dialysate discharge line 42, plunger pumps 151, 152, 153, and 154, and a synchronization motor 5.

The blood purifier 1 is a container which has inflow and outflow ports of blood and a dialysate and the inside of which is filled with hollow fibers. Due to the fact that blood is caused to pass through the internal space of the hollow fibers through the blood inflow and outflow ports and a dialysate is caused to pass through the outside of the hollow fibers through the dialysate inflow and outflow ports, removal of water from blood or backfiltration is performed.

The blood circuit 2 is connected to the blood inflow and outflow ports of the blood purifier 1. The blood circuit 2 forms a blood flow passage containing a resin tube or the like and leads blood flowing out of a blood vessel of a patient to the blood purifier 1 and leads blood flowing out of the blood purifier 1 to a blood vessel of a patient. The blood circuit 2 is provided with the blood pump 3 for generating blood flow in the blood circuit 2. For the blood pump 3, known substances, such as a tube pump, may be employed.

The dialysate line 4 is connected to the dialysate inflow and outflow ports of the blood purifier 1. The dialysate line 4 forms a dialysate flow passage containing a resin tube or the like. The fresh dialysate supply line 41 is connected to the inflow port of the blood purifier 1 and the used dialysate discharge line 42 is connected to the outflow port of the blood purifier 1. Although not illustrated in each figure, the other end of the fresh dialysate supply line 41 is connected to a tank in which a fresh dialysate is stored and the other end of the used dialysate discharge line 42 is connected to a waste tank storing a used dialysate.

In the fresh dialysate supply line 41, a part of the line between the blood purifier 1 and a tank (not illustrated) has a parallel structure in which the line is divided into two lines. In the fresh dialysate supply line 41 forming the parallel structure, plunger pumps 151 and 152 are individually disposed in the parallel lines so as to form one pair.

To the pair of plunger pumps 151 and 152, rotation is transmitted through a drive joint 6 (an example of the first drive joint) from a rotation shaft 50 of the synchronization motor 5. The drive joint 6 is connected to one end side of plungers 161 and 162 of the plunger pumps 151 and 152, respectively. The plungers 161 and 162 reciprocate in cylinders 171 and 172, respectively, by drive transmitted from the drive joint 6. Axial directions 191 of the plungers 161 and 162 incline (cross) with respect to an axial direction 193 of the drive joint 6. The strokes of the plungers 161 and 162 which reciprocate by drive transmitted from the drive joint 6 are determined depending on the inclination angle $\theta$ between the axial directions 191 of the plungers 161 and 162 and the axial direction 193 of the drive joint 6. More specifically, when the inclination angle $\theta$ is large, the strokes of the plungers 161 and 162 become large and when the inclination angle $\theta$ is small, the strokes of the plungers 161 and 162 become small.

A pair of ports communicating with the internal space are provided in each of the cylinders 171 and 172. The pair of ports are disposed at positions different by 180° with respect to the axial directions of the cylinders 171 and 172, i.e., axial symmetry. Although not illustrated in detail in each figure, the plungers 161 and 162 have a columnar shape sealing the cylinder 171 and 172, respectively, in a fluid-tight manner and the half including the axis line of the columnar shape on the tip side (other end side which is not connected to the drive joint 6) is notched. Due to the fact that the notched portions rotate in the cylinders 171 and 172, one of the pair of ports of the cylinders 171 and 172 is sealed by the plungers 161 and 162, respectively, and the other port is opened by the notched portion.

Figure 8:
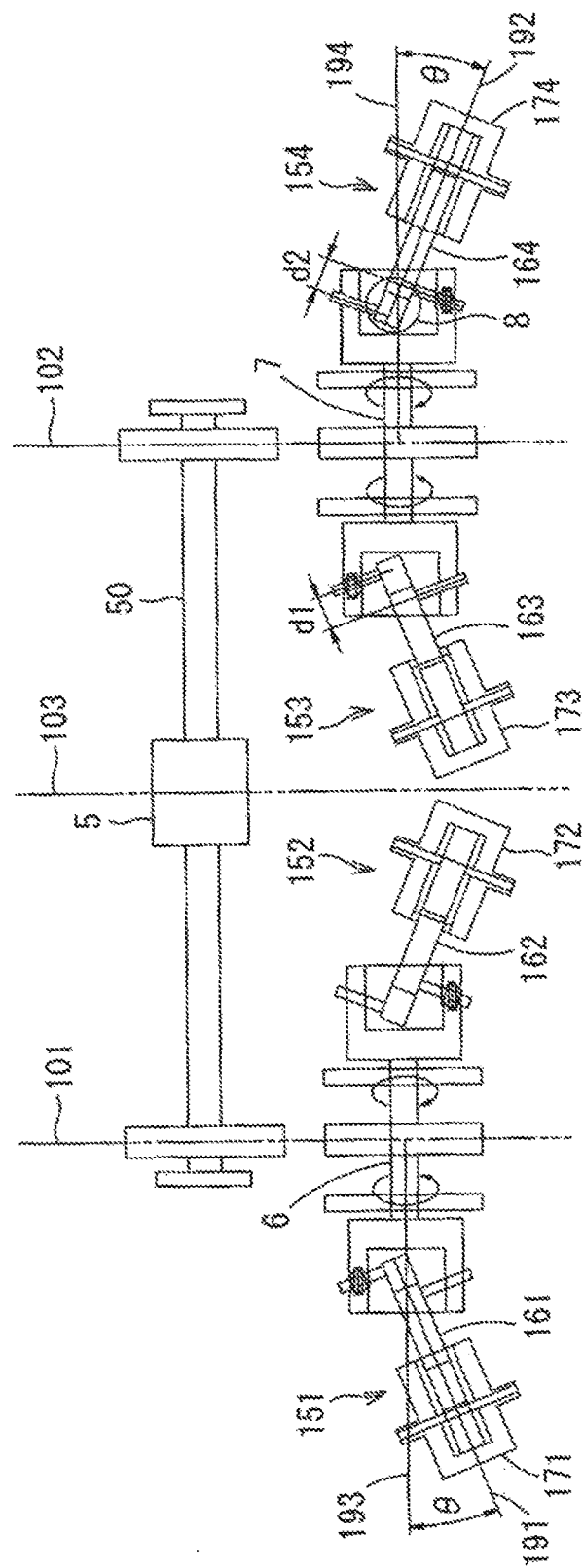
FIG. 8 is a plan view illustrating the structure of plunger pumps 51, 52, 53, and 54.
Figure 9:
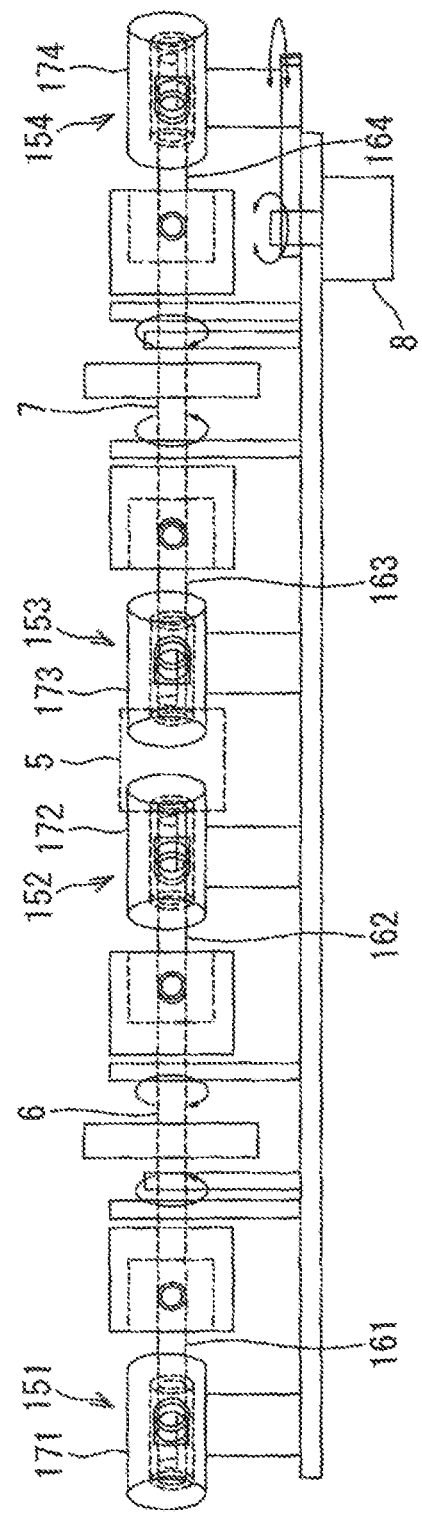
FIG. 9 is a side view illustrating the structure of the plunger pumps 51, 52, 53, and 54.

As illustrated in FIGS. 7 to 9, the one pair of plunger pumps 151 and 152 have a mirror-symmetrical structure with respect to the plane (plane orthogonal to the sheet of FIGS. 7 to 9) orthogonal to the rotation shaft 50 of the synchronization motor 5. In detail, as illustrated in FIGS. 7 and 8, the plunger pumps 151 and 152 have a mirror-symmetrical structure with respect to a plane 101 orthogonal to the rotation shaft 50 of the synchronization motor 5 and including the middle in a direction along the axial direction of the drive joint 6. Therefore, the angles at which the plungers 161 and 162 incline with respect to the drive joint 6, the positions of the ports of the cylinders 171 and 172, and the like are in a mirror-symmetrical state.

Thus, the phases of the plunger pumps 151 and 152 are different from each other by 180° with respect to the rotation of the drive joint 6. More specifically, the plunger pump 152 is sucking a fresh dialysate while the plunger pump 151 is delivering a fresh dialysate and the plunger pump 152 is delivering a fresh dialysate while the plunger pump 151 is sucking a fresh dialysate. Thus, the pair of plunger pumps 151 and 152 alternately and continuously perform the delivery of a fresh dialysate by the plunger pump 151 and the delivery of a fresh dialysate by the plunger pump 152.

In the used dialysate discharge line 42, a part of the line between the blood purifier 1 and a waste tank (not illustrated) has a parallel structure in which the line is divided into two lines. In the used dialysate discharge line 42 forming the parallel structure, plunger pumps 153 and 154 are individually disposed in the parallel lines so as to form one pair.

To the pair of plunger pumps 153 and 154, rotation is transmitted through a drive joint 7 (an example of the second drive joint) from the rotation shaft 50 of the synchronization motor 5. The drive joint 7 is connected to one end side of each of plungers 163 and 164 of the plunger pumps 153 and 154, respectively. The plungers 163 and 164 reciprocate in cylinders 173 and 174, respectively, by drive transmitted from the drive joint 7. Axial directions 192 of the plungers 163 and 164 incline (cross) with respect to an axial direction 194 of the drive joint 7. The strokes of the plungers 163 and 164 which reciprocate by drive transmitted from the drive joint 7 are determined depending on the inclination angle $\theta$ between the axial directions 192 of the plungers 163 and 164 and the axial direction 194 of the drive joint 7. More specifically, when the inclination angle $\theta$ is large, the strokes of the plungers 163 and 164 become large and, when the inclination angle $\theta$ is small, the strokes of the plungers 161 and 162 become small.

The inclination angle $\theta$ with respect to the drive joint 6 or the drive joint 7 in each of the plungers 161, 162, and 163 of each of the plunger pumps 151, 152, and 153 is fixed but the inclination angle $\theta$ with respect to the drive joint 7 of the plunger 164 of the plunger pump 154 is variable. The inclination angle $\theta$ of the plunger 164 is adjusted by the drive of the angle adjustment motor 8.

In detail, the drive joint 7 is provided with a bearing socket. To the bearing socket, a bearing is attached. The bearings each are provided with a through-hole in the central portion. One end of operation shafts extending from the plungers 163 and 164 of the plunger pumps 153 and 154, respectively, is slidably inserted into and passed through the through-holes. The operation shafts are fixed so that that the other ends thereof are perpendicular to the surface of the plungers 163 and 164. The rotation of the rotation shaft 50 of the synchronization motor 5 is transmitted to the plungers 163 and 164 through the drive joint 7 and the operation shafts and the strokes d1 and d2 are individually generated in the plunger pump 153 and 154 according to the inclination angle θ. Thus, the plungers 163 and 164 reciprocate in the strokes d1 and d2 while rotating in the cylinders 173 and 174, respectively. The same applies to the transmission of the drive to the plunger pumps 151 and 152 from the drive joint 6.

A pair of ports communicating with the internal space are provided in each of the cylinders 173 and 174. The pair of ports are disposed at positions different by 180° with respect to the axial directions of the cylinders 173 and 174, respectively, i.e., axial symmetry. Although not illustrated in detail in each figure, the plungers 163 and 164 have a columnar shape sealing the cylinders 173 and 174, respectively, in a fluid-tight manner and the half including the axis line of the columnar shape on the tip side (other end side which is not connected to the drive joint 7) is notched. Due to the fact that the notched portions rotate in the cylinders 173 and 174, one of the pair of ports of the cylinders 173 and 174 is sealed by the plungers 163 and 164, respectively, and the other port is opened by the notched portion.

As illustrated in FIGS. 7 to 9, the one pair of plunger pumps 153 and 154 have a mirror-symmetrical structure with respect to the plane (plane orthogonal to the sheet of FIGS. 7 to 9) orthogonal to the rotation shaft 50 of the synchronization motor 5. In detail, as illustrated in FIGS. 7 and 8, the plunger pumps 153 and 154 have a mirror-symmetrical structure with respect to a plane 102 orthogonal to the rotation shaft 50 of the synchronization motor 5 and including the middle in a direction along the axial direction of the drive joint 7. Therefore, the angles at which the plungers 163 and 164 incline with respect to the drive joint 7, the positions of the ports of the cylinders 173 and 174, and the like are in a mirror-symmetrical state.

Thus, the phases of the plunger pumps 153 and 154 are different from each other by 180° with respect to the rotation of the drive joint 7. More specifically, the plunger pump 154 is delivering a used dialysate while the plunger pump 153 is sucking a used dialysate and the plunger pump 154 is sucking a used dialysate while the plunger pump 153 is delivering a used dialysate. Thus, the pair of plunger pumps 153 and 154 alternately and continuously perform the suction of a used dialysate by the plunger pump 153 and the suction of a used dialysate by the plunger pump 154.

As illustrated in FIGS. 7 to 9, the pair of plunger pumps 151 and 152 and the pair of plunger pumps 153 and 154 have a mirror-symmetrical structure with respect to the plane (plane orthogonal to the sheet of FIGS. 7 to 9) orthogonal to the rotation shaft 50 of the synchronization motor 5. In detail, as illustrated in FIGS. 7 and 8, the pair of plunger pumps 151 and 152 and the pair of plunger pumps 153 and 154 have a mirror-symmetrical structure with respect to a plane 103 including the center of the rotation shaft 50 of the synchronization motor 5. Therefore, the supply of a fresh dialysate to the blood purifier 1 by the plunger pumps 151 and 152 and the discharge of a used dialysate from the blood purifier 1 by the plunger pump 153 and 154 are simultaneously performed in a synchronized manner. Thus, the pulsation of a dialysate in the supply of a fresh dialysate to the blood purifier 1 by the plunger pumps 151 and 152 and the pulsation of a dialysate in the discharge of a used dialysate from the blood purifier 1 by the plunger pumps 153 and 154 are synchronized at the same phase.

The capacities of the cylinders 171, 172, 173, and 174 and the structures of the plungers 161, 162, 163, and 164 of the plunger pumps 151, 152, 153 and 154 are the same. Therefore, when the inclination angle θ of each of the plungers 161, 162, 163, and 164 is the same, the delivery amount of a fresh dialysate or the suction amount of a used dialysate by each of the plunger pumps 151, 152, 153, and 154 is the same. However, due to the fact that the stroke d2 of the plunger 164 of the plunger pump 154 is made variable, the suction amount of a used dialysate per the stroke d2 by the plunger pump 154 can be varied so as to be different from the delivery amount of a fresh dialysate or the suction amount of a used dialysate by the other plunger pumps 151, 152, and 153. Therefore, when the stroke d2 of the plunger pump 154 is made larger than the stroke d1 of the plungers 161 and 162 on the fresh dialysate delivery side, removal of water from blood can be performed in the blood purifier 1 and, when the stroke d2 is made smaller than the stroke d1, backfiltration of blood can be performed in the blood purifier 1.

Operational Effects of Second Embodiment

According to the second embodiment, the delivery of a fresh dialysate from the plunger pump 151 and the delivery of a fresh dialysate from the plunger pump 152 are alternately and continuously performed in the pair of plunger pumps 151 and 152 provided in the parallel fresh dialysate supply lines 41, the suction of a used dialysate into the plunger pump 153 and the suction of a used dialysate into the plunger pump 154 are alternately and continuously performed in the pair of plunger pumps 153 and 154 of the parallel used dialysate discharge lines 42, and further the plunger pumps are synchronized so that the delivery of a fresh dialysate and the suction of s used dialysate simultaneously occur. Therefore, the supply of a fresh dialysate to the blood purifier 1 and the discharge of a used dialysate from the blood purifier 1 are simultaneously performed. Thus, a fresh dialysate without pulsation is supplied to the blood purifier 1.

Moreover, the stroke d2 of the plunger pump 154 of the pair of plunger pumps 153 and 154 of the parallel used dialysate discharge lines 42 is made variable. Therefore, when the stroke d2 of the plunger pump 154 provided in the used dialysate discharge line 42 is adjusted to be smaller than the strokes d1 of the plunger pumps 151 and 152 provided in the fresh dialysate supply line 41, backfiltration of blood can be performed in the blood purifier 1. When the stroke d2 of the plunger pump 154 provided in the used dialysate discharge line is adjusted to be larger than the strokes d1 of the plunger pumps 151 and 152 provided in the fresh dialysate supply line 41, removal of water from blood can be performed in the blood purifier 1.

Moreover, the pair of plunger pumps 151 and 152 are disposed in a mirror-symmetrical manner with respect to the plane 101 orthogonal to the rotation shaft 50 of the synchronization motor 5 and are individually connected to the rotation shaft 50 of the synchronization motor 5 through the drive joint 6. Therefore, the pair of plunger pumps 151 and 152 have a relationship in which the phases are 180° shifted from each other. Therefore, even when the phases of the pair of plunger pumps 151 and 152 are not adjusted, the supply of a fresh dialysate to the blood purifier 1 can be alternately and continuously performed.

Moreover, the pair of plunger pumps 153 and 154 are disposed in a mirror-symmetrical manner with respect to the plane 102 orthogonal to the rotation shaft 50 of the synchronization motor 5 and are individually connected to the rotation shaft 50 of the synchronization motor 5 through the drive joint 7. Therefore, the pair of plunger pumps 153 and 154 have a relationship in which the phases are 180° shifted from each other. Therefore, even when the phases of the pair of plunger pumps 153 and 154 are not adjusted, the discharge of a used dialysate from the blood purifier 1 can be alternately and continuously performed.

The pair of plunger pumps 151 and 152 provided in the fresh dialysate supply line 41 and the pair of plunger pumps 153 and 154 provided in the used dialysate discharge line 42 are disposed in a mirror-symmetrical manner with respect to the plane 103 orthogonal to the rotation shaft 50 of the synchronization motor 5. Therefore, the pair of plunger pumps 151 and 152 and the pair plunger pump 153 and 154 have a relationship in which the phases are 180° shifted from each other. Thus, even when the phases of the pair of plunger pumps 151 and 152 and the phases of the pair plunger pump 153 and 154 are not adjusted, the supply of a fresh dialysate to the blood purifier 1 and the discharge of a used dialysate from the blood purifier can be simultaneously performed.

Moreover, the stroke d2 of the plunger pump 154 provided in the used dialysate discharge line 42 can be adjusted by adjusting the inclination angle θ. Therefore, when the stroke d2 of the plunger pump 154 is made larger than the stroke d1 of the plunger 161 and 162 on the fresh dialysate delivery side, removal of water from blood can be performed in the blood purifier 1 and, when the stroke d2 is made smaller than the stroke d1, backfiltration of blood can be performed in the blood purifier 1.

Modification of Second Embodiment

In the second embodiment described above, the pair of plunger pumps 151 and 152 provided in the fresh dialysate supply line 41 and the pair of plunger pumps 153 and 154 provided in the used dialysate discharge line 42 are disposed in a mirror-symmetrical manner with respect to the plane 103 orthogonal to the rotation shaft 50 of the synchronization motor 5. However, even when the mirror-symmetrical manner is not always employed, the pair of plunger pumps 151 and 152 and the pair plunger pump 153 and 154 can establish a relationship in which the phases are 180° shifted from each other.

Figure 10:
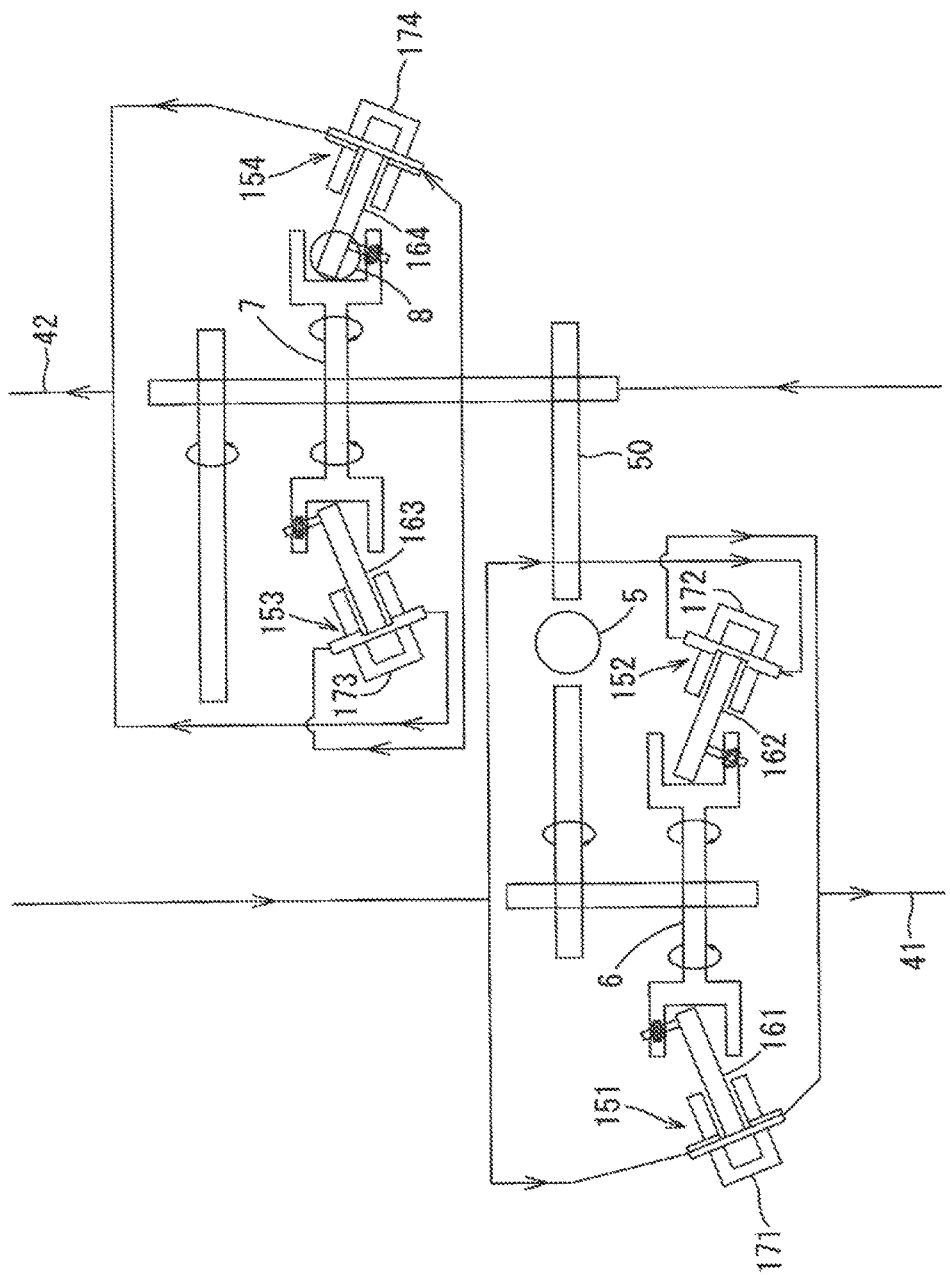
FIG. 10 is a schematic view illustrating a modification of the blood purification device 10.
Figure 11:
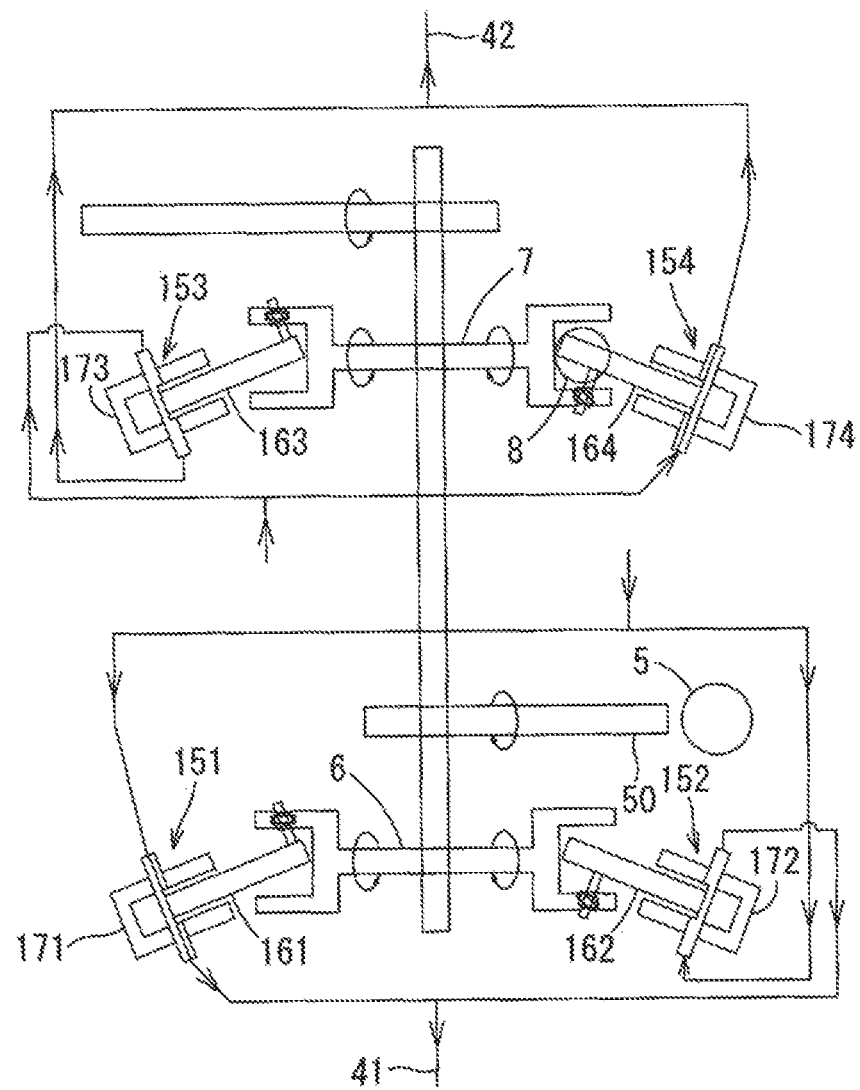
FIG. 11 is a schematic view illustrating a modification of the blood purification device 10.

For example, as illustrated in FIGS. 10 and 11, the drive joint 6 and the drive joint 7 are not disposed on one rotation axis line and are disposed to be offset to positions different from each other with respect to the rotation shaft 50 of the synchronization motor 5. However, insofar as the drive joint 6 and the drive joint 7 are disposed on one rotation axis line, the supply of a fresh dialysate to the blood purifier 1 and the discharge of a used dialysate from the blood purifier can be simultaneously performed even in the case of the mirror-symmetrical arrangement with respect to the plane 103 and even when the phases of the pair of plunger pumps 151 and 152 and the pair of plunger pumps 153 and 154 are not adjusted. Moreover, the pair of plunger pumps 151 and 152 and the pair of plunger pumps 153 and 154 can be disposed in parallel to each other instead of being disposed in series along the rotation shaft 50 of the synchronization motor 5, a reduction in size of the blood purification device 11 can be achieved. In particular, due to the fact that the pair of plunger pumps 151 and 152 and the pair of plunger pumps 153 and 154 are disposed in a perfect parallel manner as illustrated in FIG. 11, the contribution to a reduction in size of the blood purification device 11 becomes remarkable.

The invention claimed is:

1. A blood purification device comprising:
   a blood purifier;
   a blood circuit;
   a blood pump; and
   a dialysate line having a fresh dialysate supply line and a used dialysate discharge line, wherein:
   a pair of plunger pumps are disposed in the dialysate line,
   the pair of plunger pumps are synchronized so that delivery of a fresh dialysate from one plunger pump and suction of a used dialysate into the other plunger pump simultaneously occur,
   a stroke of at least one of the pair of plunger pumps is variable, and
   the pair of plunger pumps are disposed in a mirror-target manner with respect to a rotation shaft of a synchronization motor and are individually connected to the synchronization motor located in a central portion of the rotation shaft through drive joints.

2. The blood purification device according to claim 1, wherein a stroke of the plunger pump on a fresh dialysate delivery side is fixed and adjustment of a stroke of the plunger pump on a used dialysate suction side is performed by an angle adjustment motor adjusting a horizontal inclination angle between the plunger pumps and the rotation shaft of the synchronization motor.

3. The blood purification device according to claim 1, wherein
   a rotation radius of the drive joint on the used dialysate suction side is made larger than a rotation radius of the drive joint on the fresh dialysate delivery side, and
   a stroke of the plunger pump on the used dialysate suction side is made variable.

4. The blood purification device according to claim 1, wherein the plunger pump is a valveless plunger pump.

5. The blood purification device according to claim 1, wherein another pair of plunger pumps having a 180° shifted phase are disposed in parallel to the dialysate line.

6. A blood purification device comprising:
   a blood purifier;
   a blood circuit connected to the blood purifier;
   a blood pump for generating blood flow in the blood circuit;
   a synchronization motor;
   drive joints which rotate by driving force given from the synchronization motor;
   a dialysate line having a fresh dialysate supply line and a used dialysate discharge line each connected to the blood purifier; and
   plunger pumps provided, respectively, in the fresh dialysate supply line and the used dialysate discharge line so as to form one pair, wherein:
   the plunger pump provided in the fresh dialysate supply line and the plunger pump provided in the used dialysate discharge line are synchronized so that delivery of a fresh dialysate by the plunger pump provided in the fresh dialysate supply line and suction of a used dialysate by the plunger pump provided in the used dialysate discharge line are simultaneously performed, and
   the pair of plunger pumps are disposed in a mirrored, symmetrical manner with respect to a plane orthogonal to a rotation shaft of the synchronization motor and are connected to the synchronization motor by the drive joints.

7. A blood purification device comprising:
   a blood purifier;
   a blood circuit connected to the blood purifier;

a blood pump for generating blood flow in the blood circuit;

a synchronization motor;

drive joints which rotate by driving force given from the synchronization motor;

a dialysate line having a fresh dialysate supply line and a used dialysate discharge line each connected to the blood purifier; and plunger pumps provided, respectively, in the fresh dialysate supply line and the used dialysate discharge line so as to form one pair, wherein:

the plunger pump provided in the fresh dialysate supply line and the plunger pump provided in the used dialysate discharge line are synchronized so that delivery of a fresh dialysate by the plunger pump provided in the fresh dialysate supply line and suction of a used dialysate by the plunger pump provided in the used dialysate discharge line are simultaneously performed, a stroke of at least one of the plunger pumps individually provided in the fresh dialysate supply line and the used dialysate discharge line is variable, a stroke of the plunger pump provided in the used dialysate discharge line is variable, and a rotation radius of the drive joint on a used dialysate suction side is larger than a rotation radius of a drive joint on a fresh dialysate delivery side.

8. The blood purification device according to claim 7, wherein in the plunger pump in which the stroke is variable of the pair of plunger pumps, an inclination angle of a shaft of a plunger with respect to the rotation shaft of a synchronization motor is adjustable.

9. The blood purification device according to claim 7 further comprising:

an angle adjustment motor varying the inclination angle of the shaft of the plunger.

10. A method for passing a dialysate to a blood purifier using a first plunger pump and a second plunger pump, respectively provided in a fresh dialysate supply line and a used dialysate discharge line, each of the fresh dialysate supply line and the used dialysate discharge line connected to the blood purifier, the method comprising:

a delivery step of delivering a fresh dialysate to the blood purifier through the fresh dialysate supply line by transmitting rotary drive to the first plunger pump from the synchronization motor; and a suction step of sucking a used dialysate from the blood purifier through the used dialysate discharge line by transmitting rotary drive to the second plunger pump from a synchronization motor, wherein the delivery step and the step are simultaneously performed in a synchronized manner.

11. The method for passing a dialysate to a blood purifier according to claim 10, wherein the transmission of the drive of the synchronization motor to the first plunger pump in the delivery step and the transmission of the drive of the synchronization motor to the second plunger pump in the suction step are performed at a 180° shifted phase.

12. The method for passing a dialysate to a blood purifier according to claim 10, wherein a stroke length of the first plunger pump in the delivery step and a stroke length of the second plunger pump in the suction step are different.

13. A blood purification device comprising:

a blood purifier;

a blood circuit connected to the blood purifier;

a synchronization motor;

a first drive joint which rotates by driving force given from the synchronization motor;

a blood pump for generating blood flow in the blood circuit;

a dialysate line having (i) a fresh dialysate supply line coupled to a fresh dialysate tank and to the blood purifier, and (ii) a used dialysate discharge line coupled to a waste dialysate tank and to the blood purifier, each of the fresh dialysate supply line and the used dialysate discharge line divided into a respective pair of parallel lines for a respective length; and a first pair of plunger pumps provided, respectively, in each of the parallel fresh dialysate supply lines, and a second pair of plunger pumps provided, respectively, in each of the parallel used dialysate discharge lines, wherein:

the first pair of plunger pumps alternately and continuously perform delivery of a fresh dialysate by one plunger pump of the first pair of plunger pumps and delivery of a fresh dialysate by the other plunger pump of the first pair of plunger pumps, the second pair of plunger pumps alternately and continuously perform suction of a used dialysate by one plunger pump of the second pair of plunger pumps and suction of a used dialysate by the other plunger pump of the second pair of plunger pumps, the first pair of plunger pumps and the second pair of plunger pumps are synchronized so that delivery of a fresh dialysate by the first pair of plunger pumps and suction of a used dialysate by the second pair of plunger pumps are simultaneously performed, and the first pair of plunger pumps are disposed in a mirrored, symmetrical manner with respect to a plane orthogonal to a rotation shaft of the synchronization motor and are connected to the synchronization motor by the first drive joint.

14. The blood purification device according to claim 13 further comprising:

a synchronization motor; and a second drive joint which rotates by driving force given from the synchronization motor, wherein the second pair of plunger pumps are disposed in a mirrored, symmetrical manner with respect to a plane orthogonal to the rotation shaft of the synchronization motor and are connected to the synchronization motor by the second drive joint.

15. The blood purification device according to claim 14, wherein the first pair of plunger pumps and the second pair of plunger pumps are disposed in a mirrored, symmetrical manner with respect to a plane orthogonal to the rotation shaft of the synchronization motor.

* * * * *

UNITED STATES PATENT AND TRADEMARK OFFICE
CERTIFICATE OF CORRECTION

PATENT NO. : 10,307,523 B2
APPLICATION NO. : 15/123349
DATED : June 4, 2019
INVENTOR(S) : Mitsutaka Ueda et al.

Page 1 of 1

It is certified that error appears in the above-identified patent and that said Letters Patent is hereby corrected as shown below:

On the Title Page

In Column 1, below Item (65), insert -- (30) Foreign Application Priority Data.
Mar. 4, 2014     (JP) ......................2014-041441
May 15, 2014    (JP) ......................2014-101538
May 27, 2014    (JP) ......................2014-109541
May 27, 2014    (JP) ......................2014-109547
Sep. 25, 2014    (JP) ..................... 2014-195371 --

Signed and Sealed this
Eighth Day of June, 2021

Drew Hirshfeld
*Performing the Functions and Duties of the
Under Secretary of Commerce for Intellectual Property and
Director of the United States Patent and Trademark Office*